United States Patent

Coombes et al.

[11] Patent Number: 5,922,357
[45] Date of Patent: Jul. 13, 1999

[54] POLYMER MICROSPHERES AND A METHOD OF PRODUCTION THEREOF

[75] Inventors: Allan Gerald Arthur Coombes, West Bridford; Stanley Stewart Davis, The Park, both of United Kingdom; Etienne Honoré Schacht, Staden, Belgium

[73] Assignees: University of Nottingham, Nottingham, United Kingdom; University of Gent, Ghent, Belgium

[21] Appl. No.: 08/714,081

[22] PCT Filed: Mar. 27, 1995

[86] PCT No.: PCT/GB95/00686

§ 371 Date: Mar. 4, 1997

§ 102(e) Date: Mar. 4, 1997

[87] PCT Pub. No.: WO95/26376

PCT Pub. Date: Oct. 5, 1996

[30] Foreign Application Priority Data

Mar. 28, 1994 [GB] United Kingdom .................... 9406094

[51] Int. Cl.⁶ ...................................................... A61K 9/50
[52] U.S. Cl. .......................... 424/491; 424/499; 424/497; 424/493; 424/489; 424/501; 424/451; 424/78.08; 514/772.1; 514/772.3; 514/951; 514/963; 428/402.24; 428/403; 428/407; 428/402.21
[58] Field of Search ...................................... 424/499, 497, 424/493, 489, 491, 501, 451, 78.08; 514/772.1, 772.3, 951, 963; 428/402.24, 403, 407, 402.21

[56] References Cited

U.S. PATENT DOCUMENTS

| | | | |
|---|---|---|---|
| 5,468,526 | 11/1995 | Allen et al. | 428/35.4 |
| 5,545,823 | 8/1996 | Kuo et al. | 523/122 |
| 5,565,215 | 10/1996 | Gref et al. | 424/501 |
| 5,714,159 | 2/1998 | Shalaby | 424/426 |
| 5,795,864 | 8/1998 | Amstutz et al. | 514/12 |

FOREIGN PATENT DOCUMENTS

| | | |
|---|---|---|
| 0 134 660 | 3/1985 | European Pat. Off. . |
| 0 291 389 | 11/1988 | European Pat. Off. . |
| 95 03357 | 2/1995 | WIPO . |

*Primary Examiner*—Margaret W. Glass
*Attorney, Agent, or Firm*—Bacon & Thomas, PLLC

[57] ABSTRACT

The invention relates to microspheres which are suitable for biomedical uses which have a diameter in the range of 10 nm to 2 mm and which comprise a substantially spherical core particle of a non-water-soluble polymer and an outer surface layer consisting substantially of a water-soluble polymer. The water-soluble polymer is conjugated to polyethylene glycol and the non-water-soluble core particle is attached to the water-soluble polymer by the polyethylene glycol moiety. The microspheres are prepared by dissolving the non-water-soluble polymer in a suitable first solvent, dispersing the polymer solution in a solution of the PEG/water-soluble polymer conjugate and evaporating the first solvent to form microspheres in which the PEG anchors the water-soluble polymer to the core particle.

25 Claims, No Drawings

POLYMER MICROSPHERES AND A METHOD OF PRODUCTION THEREOF

The invention relates to colloidal particles, particularly polymer microspheres which are suitable for biomedical applications and to a method of producing these microspheres. The invention also relates to a method of modifying the surface of polymer microspheres and other polymer surfaces used for clinical and diagnostic applications so that they are rendered more biocompatible.

The term "microsphere" is generally employed to describe a substantially spherical particle having a diameter in the range 10 nm to 2 mm. Particles having a diameter of less than 12 m are sometimes called "nanospheres". Microspheres made from a very wide range of natural and synthetic polymers have been prepared and have found use in a variety of biomedical applications. They can be labelled with markers (labels or sensing devices) and transported through various media both in vitro and in-vivo. The labels may be chemical, fluorescent, magnetic or radio-active and thus they may, by appropriate sensing equipment, be observed when in use. They may be manufactured so that they degrade after their job is complete or they may be recovered. The sort of applications for which microspheres can be used are diagnostic screening, cell separation, immunoassays, studies of phagocytosis and blood flow, studies of cell motility, haemoperfusion and extracorporeal therapy, drug delivery devices, targeted drug delivery, cell encapsulation, endovascular embolisation and vaccines.

A major problem associated with medical uses of polymers in general is that the natural surface characteristics of the polymer favour the binding of proteins. Thus, in the case of microspheres, for example, introduced into the circulatory system, plasma components known as opsonins bind to the surface of the microsphere and render it vulnerable to phagocytosis by macrophages and other phagocytic cells of the reticulo-endothelial system. In certain in-vivo applications of microspheres it is important to retain the microspheres in the circulatory system long enough for them to discharge their function. Therefore a considerable amount of research has been carried out into methods of modifying the surface of microspheres and other polymers suitable for medical use, so as to reduce protein uptake.

The general approach has been to attempt to incorporate into the surface of these polymers, materials with hydrophilic properties which will not therefore favour the uptake of proteins. For example polyethylene glycol, polyvinyl pyrrolidone and polyethyl oxazoline have been incorporated into commonly used biomedical polymers such as polyethylene terephthalate, polyurethanes and polymethylmethacrylate (Desai et al, Biomaterials 12 1991, 144–153). This work has shown polyethylene glycol to have quite a dramatic effect in reducing protein adherence at the polymer surface.

Apart from modifying the surface of the microsphere to reduce protein uptake other alterations in the surface characteristics may be desirable such as attraction of particular molecules or ligands. The surface of a microsphere can be afforded a desired characteristic by the grafting or adsorption of particular materials, functional groups or targeting ligands.

There are various known methods for the preparation of polymeric microspheres and some of these include manipulation of the surface of the final product for a particular purpose. For example, they may be prepared directly by co-polymerisation of suitably functionalized monomers as described by Arshady in Biomaterials 14 No 1, 1993, 5–15.

It is also known from U.S. Pat. No. 4,785,030 and U.S. Pat. No. 4,734,445 to produce microspheres with a hydrophilic surface using amphiphilic di-block polymers comprising a hydrophobic tail for chemical attachment to a non-water soluble core polymer. Alternatively microspheres may be generated by dissolving a suitable polymer in a solvent, dispersing the polymer solution so formed in a second liquid immiscible with the polymer solvent so as to form a dispersed phase and a continuous phase and then evaporating and/or extracting the solvent from the dispersed phase to form the polymer microspheres. In this latter method it is known, in order to prevent the droplets from coalescing or to control the droplet size, to add a surfactant material as a stabilizer to the continuous phase. This method of microsphere production is described by Arshady in Journal of Controlled Release 17 1991, 1–22, where polyvinylalcohol, polyvinylpyrrollidone, polyoxyethylene derivatives of sorbitan fatty esters and polyoxyethylene fatty ethers are mentioned as suitable surfactant stabilizers. A similar method of microsphere production is also described in EP-A-0263490 where a high molecular weight compound of sugar origin is used to stabilize the polymer droplets in the dispersion and to control the final microsphere size.

Apart from the stabilizer other factors influence the final size of the microspheres such as the design of any vessel used for mixing the two solutions. In particular the size and shape of any baffles and also the stirrer speed will have an effect.

The present inventors have developed a method of producing microspheres using a conjugate molecule which both stabilizes the polymer droplet during removal of the solvent from the dispersed phase and allows manipulation of the surface of the microspheres so that they have desirable surface characteristics for any particular application.

In accordance with a first aspect of the invention there is provided a microsphere having a diameter in the range of from 10 nm to 2 mm, which comprises a substantially spherical core particle of a non-water-soluble polymer and an outer surface layer consisting substantially of a water-soluble polymer, said water-soluble polymer being conjugated to polyethylene glycol(PEG), in which the non-water soluble core particle is attached to the water-soluble polymer by the polyethylene glycol moiety.

Preferably the non-water soluble core particle is directly attached to the water-soluble polymer by the PEG moiety.

In accordance with another aspect of the invention there is provided a method of producing microspheres having a diameter in the range from 10 nm to 2 mm comprising a non-water-soluble polymer and a water-soluble polymer, the method comprising the steps of:

(a) forming a solution of the non-water-soluble polymer in a first solvent, said first solvent also being a solvent for polyethylene glycol but not for the water-soluble polymer;

(b) forming a solution of a conjugate of polyethylene glycol (PEG) and the water-soluble polymer in a second solvent, said second solvent being immiscible with said first solvent and being a non-solvent for the non-water-soluble polymer;

(c) mixing the two solutions formed in steps (a) and (b) above to form a dispersion of said non-water-soluble polymer and (d) evaporating and/or extracting said first solvent to form microspheres having a core of said non-water-soluble polymer and an outer surface layer consisting substantially of said water-soluble polymer wherein the outer layer is attached to the core by the polyethylene glycol moiety.

It is to be understood that the first and second solvents referred to above may in fact each independently be mixtures of solvents provided that a dispersed phase (first solvent) and a continuous phase (second solvent) is produced.

In the above described method the dispersed phase consists initially of droplets of core polymer solution in a continuous phase of PEG/water-soluble polymer conjugate solution. The PEG which is soluble in the first solvent becomes entangled with the molecules of the core polymer effectively forming a polymer blend at the surface of the droplet. This leaves the water-soluble polymer, which is insoluble in the first solvent, on the outer surface of the polymer droplet. When the first solvent is removed, the droplets contract to form microspheres entrapping the PEG conjugate with the PEG providing the anchor for the conjugate to the polymer microsphere and the water-soluble polymer protruding outwards into the continous phase.

The above represents a general theory as to how microspheres are formed in the method of the invention. However it is not discounted that the outermost layer of a microsphere so formed may include an amount of PEG while the inner surface layer may include an amount of the water-soluble polymer. In any event in the microspheres of the invention the attachment between the PEG and the non-water soluble core is substantially a physical rather than chemical one, the process of production involving chain entanglement and interpenetration rather than chemical reaction. Therefore the outer surface layer is not grafted onto the core. The possibility of the ether bonds of PEG forming hydrogen bonds with a suitable functional group on the core particle is not, however discounted.

As discussed above microspheres are useful for a variety of biomedical applications and can be made from a number of polymer materials depending on the required use. For example for certain imaging techniques where the microspheres are fluorescent, magnetic or radio-active it may be desirable to recover the microspheres. If a non-biodegradable polymer core material is required, suitable materials might be polystyrene, polyurethane and its derivatives, polyolefins such as polypropylene, non-water soluble methacrylate polymers, polyamides and copolymers of polyamides with for example polypropylene oxide.

In other applications, such as drug targeting where the microsphere is required to carry an active agent to a particular site in the human or animal body for release, a biodegradable/resorbable polymer material is preferable so that it will be broken down in the body either once the job has been done or to facilitate the release of the active agent. Suitable biodegradable polymer core materials are polyesters such as polylactide, polyglycolide, copoly-(lactide-glycolide), polyhydroxybutyrate, polycaprolactone, copolymers of lactic acid and lactone, copolymers of lactic acid and PEG, polyanhydrides, polyorthoesters, polyphosphazines, copolymers of hydroxybutyrate and hydroxyvalerate, poly (ethylene carbonate), copoly(ethylene carbonate), or polyethylene, terephthalate.

The water-soluble polymer may be selected from protein, polysaccharide and nucleic acid, whether it is natural or synthetically made and is conjugated to the PEG. Water-soluble synthetic polymers not falling in the above categories may be used such as for example, polyamidoamines, polyvinyl alcohol, polymalic acid, poly($\omega$-hydroxyalkyl) acrylates and methacrylates and copolymers containing hydroxyl containing monomer units and poly(amino acids) such as poly-L-glutamic acid, poly(benzyl L-glutamate) and poly-L-aspartic acid. It is to be understood that herein the term protein is intended to include peptides, glycoproteins, metalloproteins, lipoproteins and subunits or fragments thereof, the term polysaccharide to include polymers of amino sugars, the term nucleic acid to include oligonucleotides as small as 10 nucleotides in length and the term water-soluble polymer to include a mixture of or a conjugate of, two or more of the types of water soluble polymer listed above. Water-soluble polymers which are useful in the preparation of microspheres in accordance with the invention are polysaccharides such as dextran, chitosan, pectin, hyaluronic acid, cellulose, starch, pullulan, inulin, heparin and heparin-like synthetic polymers.

A particularly preferred polysaccharide in a PEG/polysaccharide conjugate is dextran. It is preferable if the polysaccharide has a molecular weight of from 6,000 to 200,000. Further, it is envisaged that the conjugate material for use in the invention could be a mixture of PEG/polysaccharide molecules comprising two or more of the preferred polysaccharides listed above.

PEG/polysaccharide conjugates when used in the invention, have surfactant properties. They act as a stabilizer when the microspheres are formed so as to prevent coalescence and influence their final size. In addition microspheres having a PEG/polysaccharide conjugate attached to their surface have been shown to be unexpectedly resistant to phagocytosis by cells of the reticulo-endothelial system in vitro. Methods of preparing such conjugates are describes by Duval et al in Carbohydrate Polymers 15 1991 233–242.

Alternatively, the method of the invention may be carried out using in the second solvent a conjugate of PEG with a protein having suitable properties for forming the outermost surface of a microsphere. Methods for preparing conjugates of PEG and protein are known in the art and are particularly described, for example, by Nucci et al in Advances in Drug Delivery Review 6 No 2 1981, 113–151. Further, the use of a conjugate of PEG with a nucleic acid is envisaged so that the microspheres might be useful in nucleic acid hybridization assays for example.

Finally, a conjugate of PEG with a water-soluble synthetic polymer such as those described above could be used to produce microspheres with advantageous surface properties.

It is preferred to use PEG having a molecular weight in the range from 300 to 100,000 in the PEG conjugate.

For most practical purposes the microspheres of the invention will incorporate one or more additional components apart from the core polymer material and the PEG water-soluble polymer conjugate. For introduction into the human or animal body for delivery of a pharmaceutically active agent, they can be prepared with the agent incorporated therein. For example, the active agent can be dissolved in the first or second solvent, depending on its solubility properties, so that it is entrapped within the microspheres when formed. It may then be slowly released once the microspheres are introduced into the body either through the pores of the microspheres or in the case of biodegradable materials, as a result of breakdown of the microspheres. It is also possible to attach an active agent to the outside of the microsphere once formed if this is more appropriate from a drug delivery point of view.

In addition the microspheres of the invention may be used to deliver a pharmaceutically active agent to a particular site or target in the body. In such a case the microsphere may be formed with the active agent incorporated therein and then have attached to the outer surface thereof, by means of a conjugate, a molecule recognised by and having an affinity for a particular cellular receptor in the human or animal body. Such molecules include sugar moieties or monoclonal antibodies. The PEG water-soluble polymer conjugate in this case may act as a spacer molecule enabling immobilization of other molecules to the microsphere surface or the water-soluble polymer may itself be the affinity molecule.

The microspheres of the invention can also be used for the preparation of a vaccine if an antigenic material is incorporated therein. Microspheres are also useful in biomedical imaging procedures if a substance, such as a fluorescent, magnetic, radio-active or other detectable material, is incorporated into or onto the microsphere either during or after formation as discussed above.

In carrying out the method of the invention for forming microspheres, the first solvent is either evaporated or extracted or possibly a combination of both procedures. Partial evaporation may be effected by applying reduced pressure.

A colloidal polymer particle will fall within the definition of a microsphere if it has a diameter in the range of from 10 nm to 2 mm. However microspheres with a diameter of greater than 150 μm are not really suitable for injectable preparations. Nevertheless they may be used for alternative methods of administration such as oral administration.

The choice of first and second solvent will depend on the polymer core material. Generally however the second solvent for the PEG conjugate is water and the first solvent is generally immiscible with water but capable of dissolving both the non-water-soluble core polymer and PEG. The first solvent may be selected from dichloromethane chloroform, xylene and dioxane. Mixtures of these solvents with acetone or ethyl acetate are also useful in carrying out the method of the invention.

It will be appreciated that the properties of other polymer surfaces, not necessarily microspheres, having a biomedical application, can be modified by adding a PEG/water-soluble polymer conjugate as described herein.

Therefore in accordance with a third aspect of the invention there is provided a method of altering the surface characteristics of a material or device comprising a non-water-soluble polymer which method comprises attaching to the surface of said material or device a conjugate of polyethylene glycol and water-soluble polymer wherein said conjugate is orientated such that the polyethylene glycol is anchored to said surface and said water-soluble polymer forms substantially all of the outermost layer.

The surface characteristics of a solid polymeric material or device may be altered in accordance with this third aspect of the invention by firstly dispersing the PEG/water-soluble polymer conjugate in a mixture of water and an organic solvent such as, for example, acetone or dichloromethane and then immersing the material or device in the dispersion for a set time to allow softening of the surface and interpenetration and entanglement of the PEG chains with the molecules of the polymer substrate. The material or device is then removed from the dispersion and allowed to dry or alternatively, immersed in water to cause substrate hardening and entrapment of the conjugate whereby the PEG provides the anchor for the water-soluble polymer on the outer surface. A device with a modified surface is the result.

The invention will now be described with reference to the following examples in which:

Examples 1 to 6 are comparative, demonstrating the absence of production of microspheres by the solvent evaporation method, where PEG or the polysaccharide dextran are used alone;

Examples 7 to 11 describe production of microspheres in accordance with the invention and demonstrate that microsphere size and polydispersivity can be varied by altering the composition of the PEG/dextran conjugate and the solvent system for the core polymer;

Examples 12 and 13 are concerned with stability testing of microspheres in accordance with the invention using a flocculation test and indicate a change in surface characteristics of PLG microspheres when prepared by the method of the invention;

Example 15 gives the results of a static secondary ion mass spectroscopy (SSIMS) study on microspheres made in accordance with the invention and Example 16 demonstrates the in vitro resistance to phagocytosis by rat Kupffer cells of microspheres made in accordance with the invention.

EXAMPLE 1 (COMPARATIVE)

10 ml of a 5% solution of 75:25 poly(DL lactide co-glycolide) (PLG) copolymer (MW 17.000, RG 755, Boehringer) in dichloromethane (DCM) were added over 2 minutes to 20 ml of a 10% aqueous solution of Dextran (MW 70,000, Pharmacia) which was stirred at 8000 rpm with a Silverson homogeniser. Stirring was continued for a further 4 minutes.

The suspension was agitated overnight at room temperature and normal pressure to evaporate solvent.

Only a greyish, globular slick was obtained on the beaker base. No suspension of microspheres was obtained.

EXAMPLE 2 (COMPARATIVE)

The above experiment was repeated using a series of Dextran solutions of molecular weight 11,000 19,600, 39,000 72,600 and 162,000 respectively. The 25 observations are as stated in Example 1.

EXAMPLE 3 (COMPARATIVE)

The procedure described in Example 1 was repeated but an aqueous solution of poly(ethylene glycol) PEG of molecular weight 20,000 was used instead of Dextran as the continous phase.

Within 1 hour of the start of magnetic stirring to evaporate solvent, phase separation occurred. A stable microsphere suspension was not obtained under these conditions.

EXAMPLE 4 (COMPARATIVE)

The procedure described in Example 1 was repeated with aqueous solutions of 8,000 MW PEG and 100,000 MW poly(ethylene oxide) (PEO) respectively. Rapid phase separation occurred after termination of the high speed stirring stage. After 16 hours of magnetic stirring, a polymer film had formed on the surface of the remaining liquid.

EXAMPLE 5 (COMPARATIVE)

10 ml of a 5% solution of PLG in a 50:50 solvent mixture of acetone and DCM were added over 1 minute to 20 ml of a 10% aqueous solution of PEG (20,000 MW) which was stirred at 10,600 rpm. Stirring was continued for a further 4 minutes.

Phase separation occurred within 30 minutes of the start of magnetic stirring to evaporate solvent. Film formation was observed after 16 hours. No particle suspension was obtained.

EXAMPLE 6 (COMPARATIVE)

The procedure of Example 5 was repeated using a 10% aqueous solution of 70,000 MW Dextran as the continuous phase. The observations were as described in Examples 1 and 2.

EXAMPLE 7

2.5 ml of a 2% solution of PLG in a 50:50 mixture of acetone and DCM were added over 30 seconds to 5 ml of a 5% aqueous solution of PEG-Dextran (PEG-DEX) conjugate which was stirred at 8000 rpm. Stirring was continued for a further 4 minutes. The resulting suspension was stirred with a magnetic stirrer overnight to remove solvent. The microsphere suspension obtained was stable. Microspheres were harvested by centrifuging at 10,000 rpm followed by resuspension in distilled water a total of 3 times.

The PEG-DEX conjugate was synthesised from 40,000 MW Dextran, 750 MW PEG and the degree of PEG substitution was 4%.

The size of the resulting microspheres was measured by photon correlation spectroscospy and the results are presented in Table 1. This particular sample showed high polydispersity and a large spread in particle size.

EXAMPLE 8

The experiment described in Example 7 was repeated using a 1.4% PEG substituted PEG-Dextran conjugate. The molecular weight of the PEG component was 5000, the MW of the Dextran component was 40,000.

The size and polydispersity of the resulting microspheres are listed in Table 1 and reveal both a reduction in size and improvements in polydispersity relative to the PEG-Dextran conjugate used in Example 7. (4% PEG subst., 750 MW PEG).

EXAMPLE 9

The experiment described in Example 7 was repeated using a PEG-Dextran conjugate with a 9% PEG substitution. The microsphere size, shown in Table 1, was found to be increased and the polydispersity of the sample was worse when the more highly substituted conjugate was used for microsphere preparation.

EXAMPLE 10

The experiment described in Example 7 was repeated using a PEG-Dextran conjugate with a 1.2% PEG substitution. The stirring speed was approximately 7000 rpm. Microsphere size is shown in Table 1.

TABLE 1

PLG microsphere size obtained using PEG-Dextran conjugate stabilisers and a mixed solvent system.

| Example | PEG subst. | PEG MW | Dextran MW | Particle size | Polydispersity |
|---|---|---|---|---|---|
| 7 | 4 | 750 | 40,000 | 2.4 ± 0.9 μm | — |
| 8 | 1.4 | 5000 | 40,000 | 389.0 ± 11.9 nm | 0.3 ± 0.1 |
| 9 | 9 | 5000 | 40,000 | 681.1 ± 36.1 | 0.5 ± 0.1 |
| 10 | 1.2 | 5000 | 40,000 | 481.0 ± 25.0 | 0.3 ± 0.1 |
| 11* | 1.2 | 5000 | 40,000 | 1041.2 ± 91.2 | 0.8 ± 0.1 |

*DCM used as the solvent for PLG

EXAMPLE 11

The experiment described in Example 7 was repeated but the PLG copolymer was dissolved only in DCM. This resulted in a marked increase in size and polydispersity of the resulting microspheres relative to those obtained using a 50:50 acetone: DCM mixture. (Table 1).

EXAMPLE 12

The relative stability of dispersion of microspheres to added salt (flocculation testing) provides a simple means of characterising the surface of colloidal particles and gives information on the effectiveness of various stabilising moieties. Differences in behaviour are generally explained in terms of a stronger reduction in the solvency of the stabiliser in the dispersion medium due to differences in molecular structure, molecular conformation, chain packing density and surface coverage of the stabilising moiety.

The stability of PLG microspheres produced using PEG-Dextran conjugates is summarised in Table 2 in terms of the molar concentration of NaCl required to produce flocculation in microsphere suspensions. PLG microspheres (160 nm in diameter) produced without surfactant were used as a control.

TABLE 2

Flocculation testing of PEG-Dextran stabilised PLG microspheres

| Example | PEG subst. (%) | PEG MW | Dextran MW | Particle size (nm) | NaCl conc. for flocculation (M) |
|---|---|---|---|---|---|
| PLG | — | — | — | 160 | 0.01 |
| 9 | 9 | 5000 | 40,000 | 681 | 4 |
| 10 | 1.2 | 5000 | 40,000 | 481 | 1 |
| 11* | 1.2 | 5000 | 40,000 | 1041 | 2 |

*DCM used as the solvent for PLG

EXAMPLE 13

Surfactant-free PLG microspheres of approximately 160 nm diameter were incubated overnight in a 1% aqueous solution of PEG-Dextran conjugate (1.2% PEG subst., PEG MW 5000).

The stabiliser-free microspheres and those incubated in PEG-Dextran solution were found to flocculate rapidly and extensively on addition of phosphate buffered saline solution (pH 7.4, 0.137M NaCl).

All PEG-DEX stabilised PLG systems were stable in phosphate buffered saline.

EXAMPLE 14

Zeta potential measurements are presented in Table 3 for PLG microspheres produced as described in Example 10. Surfactant-free PLG microspheres (160 and 740 nm average diameter) were included as controls. Measurements were performed in pH 7.0, 50 mM phosphate buffer.

TABLE 3

| System | PEG subst. (%) | PEG MW | Dextran MW | Particle size (nm) | Zeta potential (mV) |
|---|---|---|---|---|---|
| PLG | — | — | — | 740 | −22.8 ± 0.8 |
| PLG | — | — | — | 160 | −23.4 ± 2.0 |
| 10 | 1.2 | 5000 | 40,000 | 481 | −8.5 ± 0.2 |

A decrease in the Zeta potential for PEG-Dextran stabilised PLG microspheres relative to surfactant-free microspheres is evident, indicating surface modification by PEG-Dextran molecules.

EXAMPLE 15

Static secondary ion mass spectroscospy (SSIMS) studies have been carried out on 1) PEG-Dextran conjugates 2) surfactant-free PLG microspheres 3) PEG and 4) PLG microspheres stabilised by PEG-Dextran conjugates. While the SSIMS spectra may not be considered quantitative, the changes in the relative intensities of the ions within the SSIMS spectra have been shown to reflect composition in a semi-quantitative way.

The peak at m/z 45 in the positive ion spectrum is strong in PEG and in PLG and weak in Dextran. This same peak is dominant in the SSIMS spectrum of PEG-DEX conjugates (Table 4). The peak at m/z 53 is strong in Dextran, present in PLG and extremely weak in PEG (Table 4).

The 53/45+53 peak ratios presented in Table 4 reveals the contribution of Dextran to the PEG-Dextran spectrum through the increased presence of m/z 53 ions characteristic of Dextran.

TABLE 4

Peak height ratios for PLG microspheres stabilised with PEG-Dextran conjugates and component polymers.

| System | Example | 53/45 + 53 |
|---|---|---|
| PEG | | 0.008 |
| PEG-DEX (1.4% subst.) | | 0.04 |
| PEG-DEX (9% subst.) | | 0.02 |
| PLG/P-D (1.4% subst.) | 8 | 0.22 |
| PLG/P-D (9% subst.) | 9 | 0.18 |
| PLG microspheres (surfactant free) | | 0.5 |
| Dextran | | 0.6 |

The peak ratios in Table 4 reflect the increasing prominence of the m/z 53 ion in the SSIMS spectrum of PEG-Dextran stabilised microspheres relative to the conjugate. This cannot be assigned unequivocally to increased surface exposure of Dextran because of the presence of the same ions in the SSIMS spectrum of PLG. Surface modification of PLG microspheres by PEG-Dextran is however indicated.

EXAMPLE 16

PLG microspheres of approximately 150 nm diameter were prepared using a nanoprecipitation method (Fessi, H., Devissaguet, J. P. Puiseux, F., Thies, C., Procede de preparation de systemes colloideum dispersibles d'une substance sous forme de nanoparticles. Centre National de la Recherche Scientifique (CNRS), Patent Application filed Dec. 31st 1986, Application No 2,608,988) in the presence of PEG-Dextran conjugate as a surface modifier (1.4% PEG subst., PEG MW 5000, Dextran MW 40,000). In-vitro studies of particle interaction with isolated rat Kupffer cells gave the following results.

TABLE 5

| | % uptake of particles | |
|---|---|---|
| System | Absence of serum | Presence of serum |
| Unmodified PLG particles | 77.0 ± 2.1 | 31.6 ± 4.6 |
| PEG-Dex modified PLG | 5.5 ± 0.9 | 1.9 ± 0.4 |

Modification of PLG nanoparticles with PEG-Dextran conjugates reduces their uptake of phagocytic cells in-vitro and could reduce sequestration of colloidal particles by the cells of the reticuloendothelial system in-vivo. Improvements in drug delivery and drug targeting could result.

We claim:

1. A microsphere having a diameter in the range from 10 nm to 2 mm, which comprises a substantially spherical core particle of a non-water-soluble polymer and an outer surface layer consisting substantially of a water-soluble polymer, said water-soluble polymer being conjugated to polyethylene glycol, wherein said non-water-soluble core particle is non-covalently attached to said water-soluble polymer by the polyethylene glycol moiety.

2. A microsphere as claimed in claim 1 wherein said non-water-soluble polymer is biodegradable or resorbable.

3. A microsphere as claimed in claim 2 wherein said biodegradable or resorbable non-water-soluble polymer is a polyester selected from the group consisting of polylactide, polyglycolide, copoly(lactide-glycolide), polyhydroxybutyrate, polycaprolactone, a copolymer of lactic acid with lactone, a copolymer of lactic acid and polyethylene gylcol (PEG) polyanhydride, polyorthoester, polyphosphazine, a copolymer of hydroxybuterate and hydroxyvalerate, poly(ethylene carbonate)copoly(ethylene propylene carbonate), polyethylene terephalate, polyalkylcyanoacrylate or a mixture of two or more thereof.

4. A microsphere as claimed in claim 1 wherein said water-soluble polymer is a protein, polysaccharide or nucleic acid.

5. A microsphere as claimed in claim 4 wherein said water-soluble polymer is a polysaccharide selected from the group consisting of dextran, chitosan, pectin, hyaluronic acid, cellulose, starch, pullulan, inulin, heparin and heparin-like synthetic polymer.

6. A microsphere as claimed in claim 5 wherein the molecular weight of the polysaccharide is in the range from 6,000 to 200,000.

7. A microsphere as claimed in claim 1 wherein the molecular weight of the polyethylene glycol is in the range from 300 to 100,000.

8. A microsphere as claimed in claim 1 which includes a pharmaceutically active agent.

9. A microsphere as claimed in claim 8 which has attached to the surface thereof a molecule recognised by and having an affinity for a cellular receptor in the human or animal body.

10. A microsphere as claimed in claim 1 which includes an antigenic material.

11. A microsphere as claimed in claim 1 which includes a material which is detectable by a biomedical imaging procedure.

12. A pharmaceutical composition which comprises a plurality of microspheres as claimed in claim 8 and a pharmaceutically acceptable carrier or diluent.

13. A vaccine which comprises a plurality of microspheres as claimed in claim 10 and a pharmaceutically acceptable carrier or diluent.

14. A method of producing microspheres having a diameter in the range of 10 nm to 2 mm comprising a non-water-soluble polymer and water-soluble polymer, the method comprising the steps of:

(a) forming a solution of the non-water-soluble polymer in a first solvent, said first solvent also being a solvent for polyethylene glycol but not for the water-soluble polymer;

(b) forming a solution of a conjugate of polyethylene glycol and the said water-soluble polymer in a second solvent, said second solvent being immiscible with said first solvent and being a non-solvent for the non-water-soluble polymer;

(c) mixing the two solutions formed in steps (a) and (b) above to form a dispersion of said non-water-soluble polymer; and (d) evaporating and/or extracting said first solvent to form microspheres having a core of said non-water-soluble polymer and an outer surface layer consisting substantially of said water-soluble polymer wherein the outer layer is non-covalently attached to the core by the polyethylene glycol moiety.

15. A method as claimed in claim 14 wherein evaporation of said first solvent is effected by applying reduced pressure.

16. A method as claimed in claim 14 or claim 15 wherein said non-water-soluble polymer is a biodegradable or resorbable polyester selected from the group consisting of polylactide, polyglycolide, copoly(lactide glycolide), polyhydroxybutyrate, polycaprolactone, a copolymer of lactic acid with lactone, a copyolymer of lactic acid with polyethylene glycol (PEG), polyanhydride, polyorthoester, polyphosphazine, a copolymer of hydroxybuterate and hydroxyvalerate, poly(ethylene carbonate)copoly(ethylene, propylene carbonate), polyethylene terephthalate, polyalkylcyanocrylate or a mixture of two or more thereof.

17. A method as claimed in claim 14 wherein said water-soluble polymer is a protein, polysaccharide or nucleic acid.

18. A method as claimed in claim 17 wherein the polysaccharide is selected from the group consisting of dextran, chitosan, pectin, hyaluronic acid, cellulose, starch, pullulan, inulin, heparin and heparin-like synthetic polymer.

19. A method as claimed in claim 17 wherein the molecular weight of the polysaccharide is in the range from 6,000 to 200,000.

20. A method as claimed in claim 14 wherein said first solvent is selected from dichloromethane, chloroform, xylene and dioxane or a mixture of the solvents with acetone or ethyl acetate.

21. A method as claimed in claim 14 wherein said second solvent is water.

22. A method as claimed in claim 14 wherein the molecular weight of the polyethylene glycol is in the range from 300 to 100,000.

23. A method as claimed in claim 14 wherein said first solvent or said second solvent or both has dissolved or dispersed therein a pharmaceutically active agent.

24. A microsphere as claimed in claim 1, wherein the non-covalent attachment of the polyethylene glycol chains is by physical entanglement to interpenetrate the polymer core so as to provide an anchor for hydrophilic species.

25. A method of altering the surface characteristics of a material or device comprising a non-water-soluble polymer which method comprises attaching to the surface of said material or device a conjugate of polyethylene glycol and a water-soluble polymer wherein said conjugate is orientated such that the polyethylene glycol is non-covalently anchored to said surface and said water-soluble polymer forms substantially all of the outermost layer.

* * * * *